(12) United States Patent
Patel

(10) Patent No.: US 9,603,930 B2
(45) Date of Patent: Mar. 28, 2017

(54) LIQUID BENDAMUSTINE FORMULATION

(71) Applicant: Mahendra R. Patel, Milltown, NJ (US)

(72) Inventor: Mahendra R. Patel, Milltown, NJ (US)

(73) Assignee: Navinta, LLC, Ewing, NJ (US)

( * ) Notice: Subject to any disclaimer, the term of this patent is extended or adjusted under 35 U.S.C. 154(b) by 0 days.

(21) Appl. No.: 14/959,651

(22) Filed: Dec. 4, 2015

(65) Prior Publication Data

US 2016/0158362 A1 Jun. 9, 2016

Related U.S. Application Data

(60) Provisional application No. 62/087,512, filed on Dec. 4, 2014.

(51) Int. Cl.

| | | |
|---|---|---|
| *A61K 31/415* | (2006.01) | |
| *A61K 47/20* | (2006.01) | |
| *A61K 31/4184* | (2006.01) | |
| *A61K 9/08* | (2006.01) | |
| *A61K 47/18* | (2017.01) | |
| *A61K 47/10* | (2017.01) | |

(52) U.S. Cl.
CPC ............ *A61K 47/20* (2013.01); *A61K 9/08* (2013.01); *A61K 31/4184* (2013.01); *A61K 47/10* (2013.01); *A61K 47/18* (2013.01)

(58) Field of Classification Search
USPC ........................................ 514/394
See application file for complete search history.

(56) References Cited

U.S. PATENT DOCUMENTS

| | | |
|---|---|---|
| 8,344,006 B2 | 1/2013 | Drager et al. |
| 8,436,190 B2 | 5/2013 | Brittain et al. |
| 8,461,350 B2 | 6/2013 | Brittain et al. |
| 8,609,707 B2 | 12/2013 | Palepu et al. |
| 8,609,863 B2 | 12/2013 | Brittain et al. |
| 8,669,279 B2 | 3/2014 | Cooper et al. |
| 8,791,270 B2 | 7/2014 | Brittain et al. |
| 2013/0041004 A1* | 2/2013 | Drager .................. A61K 9/08 514/394 |
| 2013/0210879 A1 | 8/2013 | Palepu et al. |

FOREIGN PATENT DOCUMENTS

| | | | |
|---|---|---|---|
| DE | 159289 A1 | | 3/1983 |
| DE | 159877 A1 | | 4/1983 |
| WO | WO2010036702 | * | 4/2010 |

OTHER PUBLICATIONS

R.J.Sengwa, et. al, "Dielectric properties and hydrogen bonding interaction behavior in binary mixtures of glycerol with amides and amines", Fluid Phase Equililbria 266, (2008) 54-58.
Florence Mottu, et. al., "Organic solvents for pharmaceutical parenterals and embolic liquids: A review of toxicity data", PDA Journal of Pharmaceutical Science and Technology. Nov.-Dec. 2000;54(6):456-69. (1 page abstract only).
Package insert for TREANDA® (Bendamustine hydrochloride) injection, for intravenous infustion. 6 pages.
Ribomustin® Bendamustine HCl product monograph, updated on Jan. 2002, http://www.ribosepharm.de/pdf/ribomustin_bendamustin/productmonograph.pdf. (30 page pdf. submitted).

* cited by examiner

*Primary Examiner* — Rei-Tsang Shiao
(74) *Attorney, Agent, or Firm* — St. Onge Steward Johnston and Reens, LLC

(57) ABSTRACT

The present invention provides stable bendamustine-containing pharmaceutical compositions suitable for long term storage. The compositions include bendamustine, a pharmaceutically acceptable salt, and/or a hydrate form thereof, a solvent mixture of N,N-dimethylacetamide and glycerin, and an antioxidant. The bendamustine-containing compositions have less than about 2% of total impurities after two month storage at 25° C./60% RH. The pharmaceutical compositions may be used for treating neoplastic diseases.

20 Claims, No Drawings

LIQUID BENDAMUSTINE FORMULATION

FIELD OF THE INVENTION

The present relates to a pharmaceutical formulation of bendamustine or a pharmaceutically acceptable salt and/or hydrate thereof.

BACKGROUND OF THE INVENTION

Bendamustine is one species of nitrogen mustards. It has the chemical name: 4-[5-[bis(2-chloroethyl)amino]-1-methylbenzimidazol-2-yl]butanoic acid, with the following structure (Formula I):

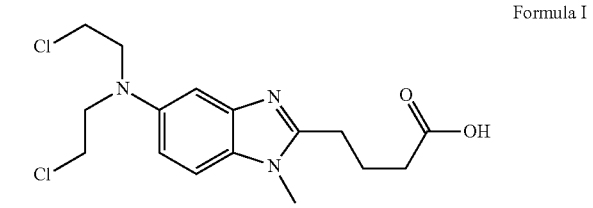 [SMILES: Cn1c(CCCC(=O)O)nc2cc(N(CCCl)CCCl)ccc21]

Bendamustine was initially synthesized in 1963 in the German Democratic Republic and was available under the name 'Cytostasan'. Bendamustine received its first marketing approval in Germany, where it is marketed under the tradename Ribomustin®. It was indicated as a single-agent or in combination with other anti-cancer agents for a number of cancers including leukemia, Hodgkin's disease, and multiple myelomas. Bendamustine is the active ingredient of the commercial drug product Treanda®, a lyophilized powder for reconstitution. Treanda® is approved by U.S. FDA for the treatment of chronic lymphocytic leukemia and indolent B-cell non-Hodgkin lymphoma that has progressed during or within six months of treatment with rituximab or a rituximab-containing regimen.

Bendamustine is a white to off-white, water soluble microcrystalline powder with amphoteric properties. Bendamustine and its salts are not stable in water. In aqueous solutions, bendamustine and its salts rapidly hydrolyze by direct substitution, leading to three main degradation impurities: a monohydroxy compound (Formula II) (the main degradant), a dihydroxy compound (Formula III), and rarely, a dimer compound (Formula IV), with the following structures:

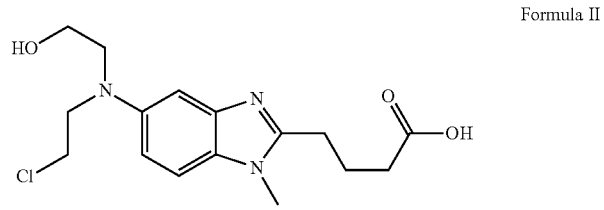

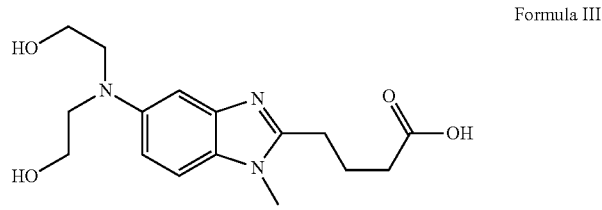

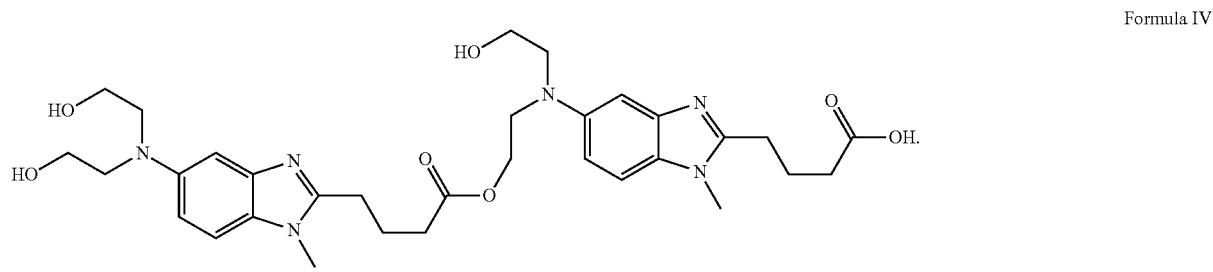

For this reason, bendamustine and its salts are not suitable for long-term storage in an aqueous solution form. Bendamustine in a solid form has improved chemical stability. The commercial product, Treanda®, is supplied as a sterile non-pyrogenic lyophilized powder in a single-use sealed vial. Each 25-mg vial contains 25 mg of bendamustine hydrochloride and 42.5 mg of mannitol, USP. Each 100-mg vial contains 100 mg of bendamustine hydrochloride and 170 mg of mannitol, USP. Prior to use, the vial is opened and reconstituted with 5 mL or 20 mL of Sterile Water for Injection, USP, and further diluted with either 0.9% Sodium Chloride Injection, USP, or 2.5% Dextrose/0.45% Sodium Chloride Injection, USP, to form a reconstituted solution with a concentration of bendamustine HCl between 0.2 mg/mL and 0.6 mg/mL. The reconstituted solution should be administrated to a patient within 30 minutes because bendamustine undergoes rapid degradation upon reconstitution, producing substantially the same main degradants (Formulas II to IV). Any unused solution should be discarded according to institutional procedures for antineoplastics.

Lyophilized bendamustine compositions are disclosed in U.S. Pat. Nos. 8,436,190, 8,461,350, 8,609,863 and 8,791,270, of the same patent family, the teachings of which are incorporated herein by reference. The patents provide methods of producing lyophilized bendamustine compositions suitable for pharmaceutical drug uses. The methods comprise the step of lyophilizing a pharmaceutical composition containing bendamustine or bendamustine hydrochloride, mannitol, water, and a solvent selected from ethanol, n-propanol, n-butanol, t-butanol (a.k.a., tert-butyl alcohol, or TBA), isopropanol, methanol, ethyl acetate, dimethyl carbonate, acetonitrile, dichloromethane, methyl ethyl ketone, methyl isobutyl ketone, acetone, 1-pentanol, methyl acetate, carbon tetrachloride, dimethyl sulfoxide, hexafluoroacetone, chlorobutanol, dimethyl sulfone, acetic acid, cyclohexane, and a combination thereof. However, the patents teach 30% TBA in water as the only solvent system that produces an acceptable lyophilate capable to be reconstituted within 3-5 minutes. Reconstitution of a lyophilate from other solvent systems is difficult and may take more than 45 minutes, which is unacceptable because the bendamustine aqueous mixture may partially degrade. But the lyophilization method using a composition having 30% TBA is not ideal because the lyophilized pharmaceutical compositions may contain a trace amount of t-butanol and up to 0.9% of the monohydroxy degradation byproduct upon reconstitution. Moreover, the lyophilized pharmaceutical compositions may additionally contain bendamustine esters as impurities.

Not all bendamustine and its pharmaceutical salts in a solid form are stable. It is reported that solid anhydrous bendamustine HCl, the form stored in Treanda® vials, may not be stable depending on how it is prepared and stored. U.S. Pat. No. 8,669,279 discloses that solid anhydrous bendamustine hydrochloride degrades after 2 months of storage at 25° C.

Bendamustine compositions in a non-aqueous liquid form for lyophilization or long term storage have been disclosed. German Patent No. 159289 reports that a propylene glycol solution of bendamustine HCl in the presence of an inert gas shows reasonable stability. But such report was recently challenged by U.S. Application Publication No. 20130210879, which discloses that a composition containing bendamustine and propylene glycol shows multiple impurities.

In U.S. Pat. No. 8,344,006, a bendamustine HCl formulation is prepared by solubilizing the drug in a solvent mixture of N,N-dimethylacetamide (also known as N,N-DMA or DMA) and propylene glycol. It shows that a solution of bendamustine in propylene glycol significantly degrades upon standing at room temperature but the addition of propylene glycol is necessary to improve the solubility of bendamustine in the solvent mixture. A solution of bendamustine HCl in N,N-dimethylacetamide is relatively stable. A preferred formulation is bendamustine HCl in a solvent mixture of 66% N,N-DMA and 34% propylene glycol.

In U.S. Pat. No. 8,609,707, a bendamustine HCl liquid formulation is prepared by solubilizing the drug in polyethylene glycol (PEG) and propylene glycol (PG). The patent discloses that the stability of the resulting formulation is improved by adding an antioxidant. Bendamustine is poorly soluble in PEG alone. There is also a risk of freezing and precipitation of the drug product at or below room temperature since the melting point of PEG is near room temperature. To mitigate the technical issues, PG is added. While a higher concentration of PG improves the solubility, it significantly decreases the stability of the formulation. To balance solubility and stability of the formulation, only a small percent of propylene glycol is presented in the solvent mixture.

There is a need for liquid bendamustine formulations which have better stability and impurity profiles than the liquid bendamustine formulations currently available.

SUMMARY OF THE INVENTION

The present invention provides a novel liquid bendamustine formulation with very good stability and impurity profile, which is particularly suitable for long term storage.

The liquid bendamustine formulation comprises (i) bendamustine, a pharmaceutically acceptable salt, and/or a hydrate form thereof, (ii) a pharmaceutically acceptable solvent system comprised of N,N-dimethylacetamide and glycerin, and optionally (iii) an antioxidant.

Preferably, the liquid bendamustine formulation is prepared from bendamustine hydrochloride or its hydrate thereof. More preferably, the liquid bendamustine formulation is prepared from bendamustine hydrochloride monohydrate. In some embodiments, bendamustine free base is in an amount of about 2% to about 10% of the total weight of the pharmaceutical composition based on actual weight of bendamustine, or calculated weight of bendamustine if bendamustine salt and/or hydrate is used.

The pharmaceutically acceptable solvent system may comprise about 5% v/v of glycerin to about 60% v/v of glycerin. Preferably, glycerin is about 10% v/v to about 50% v/v; more preferably, glycerin is about 15% v/v to about 40% v/v. In one embodiment, glycerin is about 15% v/v in the pharmaceutically acceptable solvent system; and in another embodiment, glycerin is about 28% v/v in the pharmaceutically acceptable solvent system, with the remaining solvent being N,N-dimethylacetamide.

Suitable antioxidants may include monothioglycerol, thioglycerol, lipoic acid, propyl gallate, methionine, cysteine, metabisulfites, sodium formaldehyde sulfoxylate, phenol-containing aromatic and aliphatic compounds or dihydrolipoic acid. Preferably, the antioxidant is monothioglycerol. The antioxidant may be in an amount of from about 0.2% to about 2.0%, preferably from about 0.25% to about 1.0% by weight of the composition.

The liquid bendamustine formulation has less than about 2% of total impurities after two month storage under a stress condition of 25° C. and 60% relative humidity (25° C./60% RH). The pharmaceutical formulation can be used for treating any disease that is sensitive to the treatment with bendamustine, such as neoplastic diseases.

DETAILED DESCRIPTION OF THE INVENTION

The present invention provides a bendamustine-containing pharmaceutical composition comprising glycerin and N,N-dimethylacetamide, and optionally, an antioxidant. The source of bendamustine in the bendamustine-containing pharmaceutical composition may be bendamustine free base, its pharmaceutically acceptable salts, and/or various hydrate forms. Preferably, the pharmaceutical composition includes bendamustine hydrochloride. More preferably, the pharmaceutical composition includes bendamustine hydrochloride monohydrate.

Compared to anhydrous bendamustine hydrochloride, bendamustine hydrochloride monohydrate is a better choice to be used in the preparation of bendamustine liquid formulations. As stated previously, anhydrous bendamustine HCl is unstable and may convert to hydrates upon storage in a solid form. In contrast, bendamustine hydrochloride monohydrate has a better impurity profile than anhydrous bendamustine hydrochloride and is more readily accessible in pure form (e.g., without residual solvents). Bendamustine hydrochloride monohydrate may be used directly to prepare a ready for use or ready for further dilution pharmaceutical formulation without the need to lyophilize bendamustine HCl prior to the formulation.

By the term "bendamustine-containing" formulations or compositions, it refers to all formulations or compositions that are prepared from bendamustine free base, its pharmaceutically accepted salts, and/or hydrates thereof. By the term "formulations of bendamustine HCl", it refers to all formulations or compositions prepared from bendamustine HCl and/or hydrates of bendamustine HCl.

Based on an actual or calculated weight of bendamustine free base in the pharmaceutical composition (regardless whether the source of bendamustine is a bendamustine salt and/or hydrate form), the bendamustine concentration of the pharmaceutical composition is from about 10 mg/mL to about 100 mg/mL, preferably from about 25 mg/mL to about 90 mg/mL, more preferably from about 50 mg/mL to about 90 mg/mL, and even more preferably about 90 mg/mL.

A novel feature of the pharmaceutical composition is the use of glycerol in combination with N,N-dimethylacetamide as a co-solvent system which not only increases solubility of the drug (i.e., bendamustine, its pharmaceutically acceptable salts, and/or various hydrate forms) but also improves the stability of the resulting solution. As a result, the inventive liquid composition has substantially improved long term stability when compared to currently available formulations.

In some embodiments, the co-solvent system comprises about 5% v/v to about 60% v/v of glycerin. The co-solvent system preferably comprises about 10% v/v to about 50% v/v of glycerin, more preferably comprises about 15% v/v to about 40% v/v of glycerin. In one embodiment, glycerin is about 15% v/v in the pharmaceutically acceptable solvent system; and in another embodiment, glycerin is about 28% v/v in the pharmaceutically acceptable solvent system, with the remaining solvent being N,N-dimethylacetamide.

The term "% v/v" (also written as "v/v %") means the volume of a solute in the total volume of solution. As one skilled in the art would understand, when the solute is a liquid sometimes, it is convenient to express its concentration in volume/volume percent. The calculation of "% v/v" is:

$$\text{Concentration solute (v/v \%)} = \frac{\text{volume solute (mL)}}{\text{Total volume of solution (mL)}} \times 100$$

Glycerol is a colorless, odorless, and viscous liquid. It has three hydroxyl groups in its chemical structure. As a result, it has superior solubility in water and is also hygroscopic. Bendamustine has very high solubility in glycerin. However, all the work involving alcoholic solutions of bendamustine in the prior art suggests that glycerin would not be suitable for formulating liquid bendamustine products because glycerin, which has three hydroxy groups, would likely cause more degradations than alcohols having one hydroxy or two hydroxy groups in their chemical structures. Indeed, a glycerin solution of bendamustine HCl shows significant degradation (70% degradation) upon standing at room temperature in one month. However, it is discovered by the inventor of this application that a co-solvent system of glycerin and N,N-dimethylacetamide provides excellent drug stability to bendamustine in the composition. In one embodiment, a bendamustine solution in a mixture of glycerin (which has three hydroxy groups) and N,N-dimethylacetamide forms only no more than 4% impurity after storage for two months at room temperature, the impurity level of which is less than that of a bendamustine solution in a DMA-propylene glycol (which has two hydroxy groups) mixture, as reported in U.S. Pat. No. 8,344,006.

Without wishing to be bound by theory, it is believed that the apparent decreasing in reactivity of glycerin-containing bendamustine solution (and hence the improved stability of the bendamustine solution) is due to a dipolar interaction between the hydroxyl groups of glycerin and the ketone group of N,N-dimethylacetamide. In other words, glycerin and N,N-dimethylacetamide form significant hydrogen bondings in the solution mixture. It is further believed that the hydrogen bondings cause the increase of dielectric constant of the solvent mixture, which in turn renders the solvent(s) to be less reactive. The solvent mixture of the present invention unexpectedly shows a much higher dielectric constant than each individual solvent in the mixture, probably due to the significant dipolar interactions between the two solvents in the solvent mixture. Compared to propylene glycol, glycerin has a higher dielectric constant and an extra hydroxy group in its molecular structure. Consequently, there are additional hydrogen bondings between glycerin and DMA, which further increase the dielectric constant of the solvent mixture. A solvent system having a higher dielectric constant would be able to keep the reactive center of a molecule away from other nucleophiles and thus stabilizes the molecule. Accordingly, the liquid bendamustine compositions of the present invention which contain glycerin and DMA exhibit excellent stability.

The dielectric constants at different mole fractions of glycerin in a mixture of glycerin and N,N-dimethylacetamide are tabulated below:

| Mole fraction of glycerin | Static dielectric constant ($\epsilon_{0M}$) |
| --- | --- |
| 0.000 | 37.72 |
| 0.083 | 38.22 |
| 0.164 | 39.07 |
| 0.241 | 39.80 |
| 0.316 | 40.44 |
| 0.389 | 41.04 |
| 0.459 | 41.40 |
| 0.527 | 41.83 |
| 0.592 | 42.07 |
| 0.656 | 42.33 |
| 0.718 | 42.35 |
| 0.778 | 41.84 |
| 0.836 | 41.96 |
| 0.892 | 41.88 |
| 0.947 | 41.72 |
| 1.000 | 41.17 |

(J. Sengwa, et. al, Dielectric properties and hydrogen bonding interaction behavior in binary mixtures of glycerol with amides and amines, Fluid Phase Equilibria. 266 (2008) 54-58).

As shown in the above table, the dielectric constant of a glycerin and N,N-DMA Mixture is presented in a bell shape when the mole fraction of glycerin is increased from 0% to 100% based on a mole fraction.

In alcoholic solvents, such as methanol or ethanol, the carboxylic group of bendamustine hydrochloride is easily converted to methyl or ethyl ester at room temperature.

However, when a mixture of DMA and glycerin is used as co-solvents in a bendamustine containing composition, there is only a trace amount of glycerol ester formed. It is further discovered that such bendamustine composition exhibits excellent stability even in the presence of about 1% of water in the composition (as measured by KF). It certainly is able to tolerate water (in the form of a hydrate) in bendamustine hydrochloride monohydrate. Accordingly, while the liquid bendamustine composition of the present invention is preferably substantially free of water, it may include less than about 1% of water.

The addition of an antioxidant may further contribute to the stabilization of the bendamustine-containing composition. Suitable antioxidants include, but are not limited to, monothioglycerol, thioglycerol, lipoic acid, propyl gallate, methionine, cysteine, metabisulfites, sodium formaldehyde sulfoxylate, phenol-containing aromatic and aliphatic compounds and dihydrolipoic acid. One or more antioxidants may be used in a single bendamustine-containing formulation. In some embodiments, the antioxidant used in the pharmaceutical composition of the present invention is a stabilizing amount of monothioglycerol. The term "stabilizing amount" generally refers to those amounts which increase or enhance the stability of the bendamustine in the compositions described herein. The antioxidant may be in an amount of from about 0.2% to about 2.0%, preferably from about 0.25% to about 1.0% by weight of the composition.

An impurity level of the liquid bendamustine formulation is determined by use of high performance liquid chromatography-mass spectrometry (HPLC-MS or LC-MS). As discussed before, bendamustine or its salt and/or hydrate thereof may undergo hydrolysis by direct substitution rather than an addition elimination process due to the presence of the highly labile aliphatic chlorine atoms, which leads to two main impurities: (1) the monohydroxy compound which will show in an HPLC chromatogram with a higher Relative Retention Time (RRT) and (2) the dihydroxy compound which will show in an HPLC chromatogram with a lower RRT. Bendamustine may also form esters with alcoholic solvents and form dimers, both of which are distinguishable from the monohydroxy and dihydroxy compounds by HPLC-MS. There may be some minor unknown impurities. A person of ordinary skill in the art would understand how to calculate impurity levels by calculating the ratio of impurity peak areas over the total peak areas shown in an HPLC chromatogram.

For long term storage, the liquid bendamustine pharmaceutical compositions are typically stored under a refrigerated condition (2 to 8° C.) with very low humidity. In some embodiments, bendamustine degradation impurities in the final product are less than about 1.0% under the refrigerated storage condition for two months, and less than about 4.0% under the refrigerated storage condition for six months.

To evaluate the stability of the liquid bendamustine pharmaceutical compositions, such compositions are stored under a stress condition, such as 25° C./60% RH (relative humidity). In some embodiments, the liquid pharmaceutical compositions of bendamustine HCl monohydrate contain not more than 1% of bendamustine monohydroxy impurity after it has been stored at 25° C./60% RH for two months.

The present invention further provides methods of producing such liquid bendamustine formulations. A general procedure for preparing a liquid formulation of bendamustine is set forth below. However, a person skilled in the art would understand that modifications to the procedure or process may be made.

Initially, a solvent mixture is prepared by transferring a desired amount of each solvent into a suitable container and stirring to get a clear homogenous solution. Then a desired amount of bendamustine, its pharmaceutically accepted salt and/or hydrate thereof, is weighed in a container. To the container is added approximately 70% by volume of a solvent mixture which has been prepared previously. Stir the resulting mixture for 15 minutes or until the solid dissolves. Add a desired amount of an antioxidant to the resulting solution and dilute it to a final volume by adding the solvent mixture prepared previously (approximately 30% by volume). Stir to obtain a uniform solution and filter it through a 0.22μ PVDF filter.

Impurities of the liquid bendamustine formulation are determined by running a sample of the formulation through HPLC under the following conditions:
Phase A: Water:ACN:TFA (90:10:0.1)
Phase B: Water:ACN:TFA (50:50:0.1)
Wavelength: UV, 230 nm
Flow rate: 1.0 mL/min
Column: Symmetry C-18 (250×4.6 mm) 5 μm, or equivalent
Column temperature: 25° C.
Sample temperature: 5° C.
Injection volume: 10 μL
Run time: 53 min
Diluent: Methanol In the above HPLC conditions, ACN stands for acetonitrile and TFA stands for trifluoroacetic acid. The gradient used in running the HPLC is shown in the following table:

| Time (min.) | Phase A (% v/v) | Phase B (% v/v) |
|---|---|---|
| 0.01 | 100 | 0 |
| 18 | 50 | 50 |
| 30 | 45 | 55 |
| 40 | 35 | 65 |
| 41 | 10 | 90 |
| 43 | 100 | 0 |
| 53 | 100 | 0 |

Sample preparation: dissolve the drug product with a diluent to prepare a sample for injection into HPLC, wherein the drug (i.e., bendamustine, its salt, and/or hydrate) has a concentration of 1 mg/mL. It may be necessary to perform a second dilution to reach a targeted sample concentration.

The pharmaceutical formulations can be used for any condition that is sensitive to treatment with bendamustine, such as neoplastic diseases. Accordingly, the present invention also provides a method of treating a neoplastic disease in mammals, which comprises the steps of: diluting a pharmaceutical composition of the present invention, and administering an effective amount of said diluted pharmaceutical composition to a mammal in need thereof. The neoplastic disease may be leukemia or Hodgkin's disease.

The present invention is further illustrated by the following examples:

Example 1

Two formulations of bendamustine HCl were prepared by dissolving the drug in glycerin at a concentration of 25 mg/mL. Two solutions were prepared, either with or without 1% of monothioglycerol (MTG) as an antioxidant. The solutions were filtered through a 0.22μ filter and analyzed by HPLC. The solutions were stored at 25° C./60% RH. The results from stability assays of the formulations were presented in table 1.

TABLE 1

Initial and long term stability results from Example 1.

| Solvent System | Conc. | Assay Time | Related Substances | | | |
|---|---|---|---|---|---|---|
| | | | 0.55 RRT | 0.58 RRT | Total ester | Total Impurities |
| Glycerin + 1% MTG | 25 mg/mL | Initial | 0.15 | <LOQ | 0.28 | 0.52 |
| | | 1 M@ 25° C./60% RH | 3.89 | 0.06 | 69.32 | 76.37 |
| Glycerin | 25 mg/mL | Initial | 0.03 | 0.05 | 0.14 | 0.43 |
| | | 1 M@ 25° C./60% RH | 7 | 0.58 | 59.84 | 68.59 |

1 M: 1 month
RRT: Relative Retention Time
Conc.: Concentration of Bendamustine
0.55 RRT: relative to retention time of bendamustine
0.58 RRT: relative to retention time of bendamustine
<LOQ: Limit of quantitation Table 1 shows that bendamustine containing formulations which use glycerin as the only solvent are unstable after one month storage at 25° C./60% RH, regardless whether an antioxidant is added or not.

Example 2

Two formulations of bendamustine HCl were prepared by dissolving the drug in PG at concentrations of 50 mg/mL and 90 mg/mL, respectively. To each of the solutions was added 1% of monothioglycerol (MTG) as an antioxidant. The solutions were filtered through a 0.22μ filter and analyzed by HPLC. The solutions were stored at 25° C. with 60% relative humidity (RH). The results from stability assays of the formulations were presented in table 2.

TABLE 2

Initial and long term stability results from Example 2.

| Solvent System | Conc. | Assay Time | Related Substances | | | |
|---|---|---|---|---|---|---|
| | | | 0.55 RRT | 0.58 RRT | Total ester | Total |
| PG + 1% MTG | 50 mg/mL | Initial | 0.03 | 0.05 | 0.09 | 0.22 |
| | | 1 M@ 25° C./60% RH | 0.03 | 0.04 | 5.55 | 5.85 |
| | | 2 M@ 25° C./60% RH | 0.02 | 0.04 | 24.95 | 25.48 |
| PG + 1% MTG | 90 mg/mL | Initial | 0.02 | 0.04 | 0.16 | 0.27 |
| | | 1 M@ 25° C./60% RH | 0.02 | 0.04 | 8.12 | 8.39 |
| | | 2 M@ 25° C./60% RH | 0.02 | 0.04 | 34.88 | 35.39 |

Table 2 shows that bendamustine containing formulations which use PG as a solvent with an addition of 1% of MTG as an antioxidant are relatively stable after one month storage at 25° C./60% RH, but the stability deteriorates after two month storage at 25° C./60% RH. Based on comparison of Tables 1 and 2, glycerin is an inferior solvent than propylene glycol in preparing bendamustine containing formulations. A person of ordinary skilled in the art would unlikely to select glycerin as a solvent in preparing liquid bendamustine solutions for long term storage.

Example 3

Two formulations of bendamustine HCl were prepared by dissolving the drug to a mixture of DMA: PG (66:34) at concentrations of 45 mg/mL and 90 mg/mL, respectively. The solutions were filtered through a 0.22 μL filter and analyzed. The solutions were stored at 25° C. with 60% relative humidity. The results from stability assays of the formulations were presented in table 3.

TABLE 3

Initial and long term stability results from Example 3.

| Solvent System | Conc. | Assay Time | Related Substances | | | |
|---|---|---|---|---|---|---|
| | | | 0.55 RRT | 0.58 RRT | Total ester | Total |
| DMA:PG (66:34) | 45 mg/mL | Initial | 0.04 | 0.05 | 0.03 | 0.16 |
| | | 1 M@ 25° C./60% RH | 1.67 | 0.4 | 0.95 | 2.99 |
| | | 2 M@ 25° C./60% RH | 1.88 | 0.04 | 3.19 | 5.24 |
| DMA:PG (66:34) | 90 mg/mL | Initial | 0.03 | 0.04 | 0.03 | 0.15 |
| | | 1 M@ 25° C./60% RH | 0.99 | 0.04 | 1.3 | 2.51 |
| | | 2 M@ 25° C./60% RH | 1.58 | 0.04 | 4.51 | 6.53 |

Table 3 shows that bendamustine containing formulations which use PG and DMA as co-solvents exhibit good stability after two month storage at 25° C./60% RH.

Example 4

Four formulations of bendamustine HCl were prepared by dissolving the drug in a mixture of PEG: PG (90:10) at 25 mg/mL (two formulations) and 45 mg/mL (two formulations), respectively. To each of a 25 mg/mL formulation and a 45 mg/mL formulation was added 0.5% of monothioglycerol as an antioxidant. Then to another 25 mg/mL formulation and another 45 mg/mL formulation were added 1.0% monothioglycerol as an antioxidant. The solutions were filtered through a 0.22μ filter and analyzed by HPLC. The solutions were kept at 25° C. The results from stability assays of the formulations were presented in table 4.

TABLE 4

Initial and long term stability results from Example 4.

| Solvent System | Conc. | Assay Time | Related Substances | | | |
|---|---|---|---|---|---|---|
| | | | 0.55 RRT | 0.58 RRT | Total ester | Total |
| PEG:PG (90:10) + 0.5% MTG | 25 mg/mL | Initial | 0.07 | 0.04 | 0.01 | 0.16 |
| | | 1 M@ 25° C./60% RH | 0.15 | | 1.39 | 1.65 |
| | | 2 M@ 25° C./60% RH | 0.12 | | 5.11 | 5.4 |
| PEG:PG (90:10) + 1% MTG | 25 mg/mL | Initial | 0.09 | 0.03 | 0.02 | 0.18 |
| | | 1 M@ 25° C./60% RH | 0.16 | 0.03 | 1.13 | 1.42 |
| | | 2 M@ 25° C./60% RH | 0.13 | | 4.43 | 4.77 |
| PEG:PG (90:10) + 0.5% MTG | 45 mg/mL | Initial | 0.04 | 0.03 | 0.02 | 0.13 |
| | | 1 M@ 25° C./60% RH | 0.09 | 0.03 | 1.21 | 1.4 |
| | | 2 M@ 25° C./60% RH | 0.07 | | 3.52 | 3.73 |
| PEG:PG (90:10) + | 45 mg/mL | Initial | 0.06 | 0.03 | 0.02 | 0.16 |
| | | 1 M@ | 0.09 | 0.03 | 1.22 | 1.41 |

TABLE 4-continued

Initial and long term stability results from Example 4.

| Solvent System | Conc. | Assay Time | Related Substances | | | |
|---|---|---|---|---|---|---|
| | | | 0.55 RRT | 0.58 RRT | Total ester | Total |
| 1% MTG | | 25° C./60% RH 2 M@ 25° C./60% RH | 0.08 | | 3.32 | 3.54 |

Table 4 shows that bendamustine containing formulations which use PG and PEG as co-solvents with 0.5% or 1.0% of MTG as an antioxidant agent exhibit good stability after two month storage at 25° C./60% RH.

Example 5

Two formulations of bendamustine HCl were prepared by dissolving the drug in a mixture of 85% DMA and 15% glycerin at a concentration of 90 mg/mL. To each of the formulations was added 1% monothioglycerol was added as an antioxidant. The resulting solutions were filtered through a 0.22μ filter and analyzed by HPLC. The solutions were kept at 25° C. The results from stability assays of the formulations were presented in table 5.

TABLE 5

Initial and long term stability results from Example 5.

| Solvent System | Conc. | Assay Time | Related Substances | | | |
|---|---|---|---|---|---|---|
| | | | 0.55 RRT | 0.58 RRT | Total ester | Total imp |
| DMA: Glycerin (85:15) + 1% MTG | 90 mg/mL | Initial | 0.10 | 0.04 | 0.00 | 0.18 |
| | | 1 M@ 25° C./60% RH | 0.52 | <LOQ | 0.42 | 1.42 |
| | | 2 M@ 25° C./60% RH | 0.41 | 0.05 | 0.60 | 1.88 |

Table 5 shows that bendamustine containing formulations which use DMA and glycerin as co-solvents and with 1.0% of MTG as an antioxidant agent exhibit good stability even after two month storage at 25° C./60% RH. In both of the formulations, the total impurities are less than 2.0% after two month storage at 25° C./60% RH. Compared with the results in tables 1-4, it is clear that the liquid bendamustine formulations of the present invention have superior stability and improved profiles than the prior art formulations. Moreover, the stable liquid bendamustine compositions of the present invention can be formulated at a high concentration (e.g., 90 mg/mL), which is advantageous for storage and transportation. The high concentrated liquid bendamustine compositions may be easily diluted prior to administration.

It should be noted that the invention in its broader aspects is not limited to the specific details, representative compositions, methods, and processes, and illustrative examples described in connection with the preferred embodiments and preferred methods. Modifications and equivalents will be apparent to practitioners skilled in this art and are encompassed within the spirit and scope of the appended claims.

What is claimed is:

1. A stable liquid bendamustine pharmaceutical composition comprising:
   (i) bendamustine, a pharmaceutically acceptable salt, and/or a hydrate thereof, and
   (ii) a pharmaceutically acceptable solvent system comprising N,N-dimethylacetamide and glycerin,
   wherein the pharmaceutically acceptable solvent system comprises about 5% v/v of glycerin to about 15% v/v of glycerin.

2. The pharmaceutical composition of claim 1, wherein the pharmaceutically acceptable solvent system comprises about 10% v/v of glycerin to about 15% v/v of glycerin.

3. The pharmaceutical composition of claim 2, wherein the pharmaceutically acceptable solvent system is about 15% v/v of glycerin.

4. The pharmaceutical composition of claim 1, wherein the pharmaceutical composition comprises bendamustine hydrochloride.

5. The pharmaceutical composition of claim 1, wherein the pharmaceutical composition comprises bendamustine hydrochloride monohydrate.

6. The pharmaceutical composition of claim 1, wherein bendamustine concentration is from about 10 mg/mL to about 100 mg/ml.

7. The pharmaceutical composition of claim 6, wherein the bendamustine concentration is from about 25 mg/mL to about 90 mg/mL.

8. The pharmaceutical composition of claim 7, wherein the bendamustine concentration is from about 50 mg/mL to about 90 mg/mL.

9. The pharmaceutical composition of claim 1, wherein dielectric constant of a mixture of N,N-dimethylacetamide and glycerin is higher than a mathematical average of dielectric constant of N,N-dimethylacetamide and dielectric constant of glycerin.

10. The pharmaceutical composition of claim 1, further comprising a stabilizing amount of an antioxidant, wherein the antioxidant is selected from the group consisting of monothioglycerol, thioglycerol, lipoic acid, methionine, cysteine, metabisulfites, sodium formaldehyde sulfoxylate, and dihydrolipoic acid.

11. The pharmaceutical composition of claim 10, wherein the antioxidant is monothioglycerol.

12. The pharmaceutical composition of claim 10, wherein the antioxidant is in an amount of about 0.2% to about 2.0% by weight of the pharmaceutical composition.

13. The pharmaceutical composition of claim 12, wherein the antioxidant is in amount of about 0.25% to about 1.0% by weight of the pharmaceutical composition.

14. The pharmaceutical composition of claim 1, wherein total impurities of the pharmaceutical composition after two month storage at 25° C. under 60% relative humidity are less than 2.0%.

15. The pharmaceutical composition of claim 1 comprising bendamustine hydrochloride monohydrate,
   wherein the pharmaceutically acceptable solvent system comprises about 15% v/v of glycerin and about 85% v/v of N,N-dimethylacetamide.

16. The pharmaceutical composition of claim 15, wherein the antioxidant is monothioglycerol in an amount of about 1.0% by weight of the pharmaceutical composition.

17. A method of treating a neoplastic disease in mammals, comprising:
   diluting the pharmaceutical composition of claim 1, and administering an effective amount of said diluted pharmaceutical composition to a mammal in need thereof.

18. The method of treating neoplastic diseases in mammals according to claim 17, wherein the neoplastic disease is leukemia or Hodgkin's disease.

19. A stable liquid bendamustine pharmaceutical composition comprising:
(i) a hydrate form of bendamustine or a hydrate form of bendamustine salt, and
(ii) a pharmaceutically acceptable solvent system comprising N,N-dimethylacetamide and glycerin, wherein the pharmaceutically acceptable solvent system comprises about 5% v/v of glycerin to about 60% v/v of glycerin.

20. The pharmaceutical composition of claim 19, wherein the hydrate form is bendamustine hydrochloride monohydrate.

\* \* \* \* \*